United States Patent
Liu et al.

(10) Patent No.: US 10,729,499 B2
(45) Date of Patent: Aug. 4, 2020

(54) ABLATION PLANNING SYSTEM

(75) Inventors: Xin Liu, Scarsdale, NY (US); Sandeep Delal, Cortlandt Manor, NY (US); Jochen Kruecker, Washington, DC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 875 days.

(21) Appl. No.: 14/235,140

(22) PCT Filed: Jul. 27, 2012

(86) PCT No.: PCT/IB2012/053860
§ 371 (c)(1),
(2), (4) Date: Jan. 27, 2014

(87) PCT Pub. No.: WO2013/014648
PCT Pub. Date: Jan. 31, 2013

(65) Prior Publication Data
US 2014/0201669 A1    Jul. 17, 2014

Related U.S. Application Data

(60) Provisional application No. 61/566,630, filed on Dec. 3, 2011, provisional application No. 61/514,914, filed
(Continued)

(51) Int. Cl.
*A61B 34/10* (2016.01)
*A61B 18/18* (2006.01)

(52) U.S. Cl.
CPC .......... *A61B 34/10* (2016.02); *A61B 18/1815* (2013.01); *A61B 2034/104* (2016.02); *A61B 2034/107* (2016.02)

(58) Field of Classification Search
CPC . A61B 34/10; A61B 2034/107; A61B 34/194; A61B 2017/00225; A61B 2018/00958
See application file for complete search history.

(56) References Cited

U.S. PATENT DOCUMENTS 8,758,337 B2  6/2014  Skwarek et al.
9,867,670 B2  1/2018  Brannan et al.
(Continued)

FOREIGN PATENT DOCUMENTS

| EP | 2239009 | 10/2010 |
|---|---|---|
| WO | WO2007129308 | 11/2007 |
| WO | WO2008090484 | 7/2008 |

*Primary Examiner* — Michael F Peffley
*Assistant Examiner* — Bo Ouyang
(74) *Attorney, Agent, or Firm* — Sherry Austin

(57) ABSTRACT

An ablation planning system includes a user interface (104) configured to permit selection of inputs for planning an ablation procedure. The user interface is further configured to incorporate selection of ablation probes and one or more combinations of ablation powers, durations or parameters applicable to selected probes in the inputs to size the ablation volumes. The user interface includes a display for rendering internal images of a patient, the display permitting visualizations of the ablation volumes for different entry points on the internal images. An optimization engine (106) is coupled to the user interface to receive the inputs and is configured to output an optimized therapy plan which includes spatial ablation locations and temporal information for ablation so that collateral damage is reduced, coverage area is maximized and critical structures are avoided in a planned target volume.

15 Claims, 8 Drawing Sheets

Related U.S. Application Data on Aug. 4, 2011, provisional application No. 61/512,510, filed on Jul. 28, 2011.

(56) References Cited

U.S. PATENT DOCUMENTS

| | | | |
|---|---|---|---|
| 2002/0016540 A1 | 2/2002 | Mikus et al. | |
| 2003/0050633 A1* | 3/2003 | Ellman | A61B 18/12 606/37 |
| 2008/0015664 A1 | 1/2008 | Podhajski | |
| 2008/0033420 A1* | 2/2008 | Nields | A61B 18/18 606/27 |
| 2009/0124896 A1* | 5/2009 | Haras | A61B 18/14 600/427 |
| 2009/0171203 A1* | 7/2009 | Avital | A61B 18/02 600/439 |
| 2009/0221999 A1* | 9/2009 | Shahidi | A61B 18/18 606/33 |
| 2009/0264728 A1* | 10/2009 | Fischer | A61N 5/103 600/407 |
| 2010/0019918 A1 | 1/2010 | Avital et al. | |
| 2010/0063496 A1* | 3/2010 | Trovato | G06T 7/0012 606/34 |
| 2010/0114094 A1* | 5/2010 | Thapliyal | G06F 19/321 606/41 |
| 2010/0121316 A1* | 5/2010 | Weese | G06T 7/0046 606/1 |
| 2011/0015628 A1* | 1/2011 | Dalal | A61B 18/1477 606/34 |
| 2011/0208055 A1* | 8/2011 | Dalal | A61N 7/02 600/439 |
| 2011/0251607 A1* | 10/2011 | Kruecker | A61B 18/1206 606/34 |
| 2012/0189998 A1* | 7/2012 | Kruecker | G09B 23/286 434/272 |
| 2012/0277763 A1* | 11/2012 | Greenblatt | A61B 34/10 606/130 |
| 2013/0184700 A1* | 7/2013 | Dalal | A61B 18/1206 606/33 |
| 2016/0317229 A1* | 11/2016 | Girotto | A61B 34/20 |

* cited by examiner

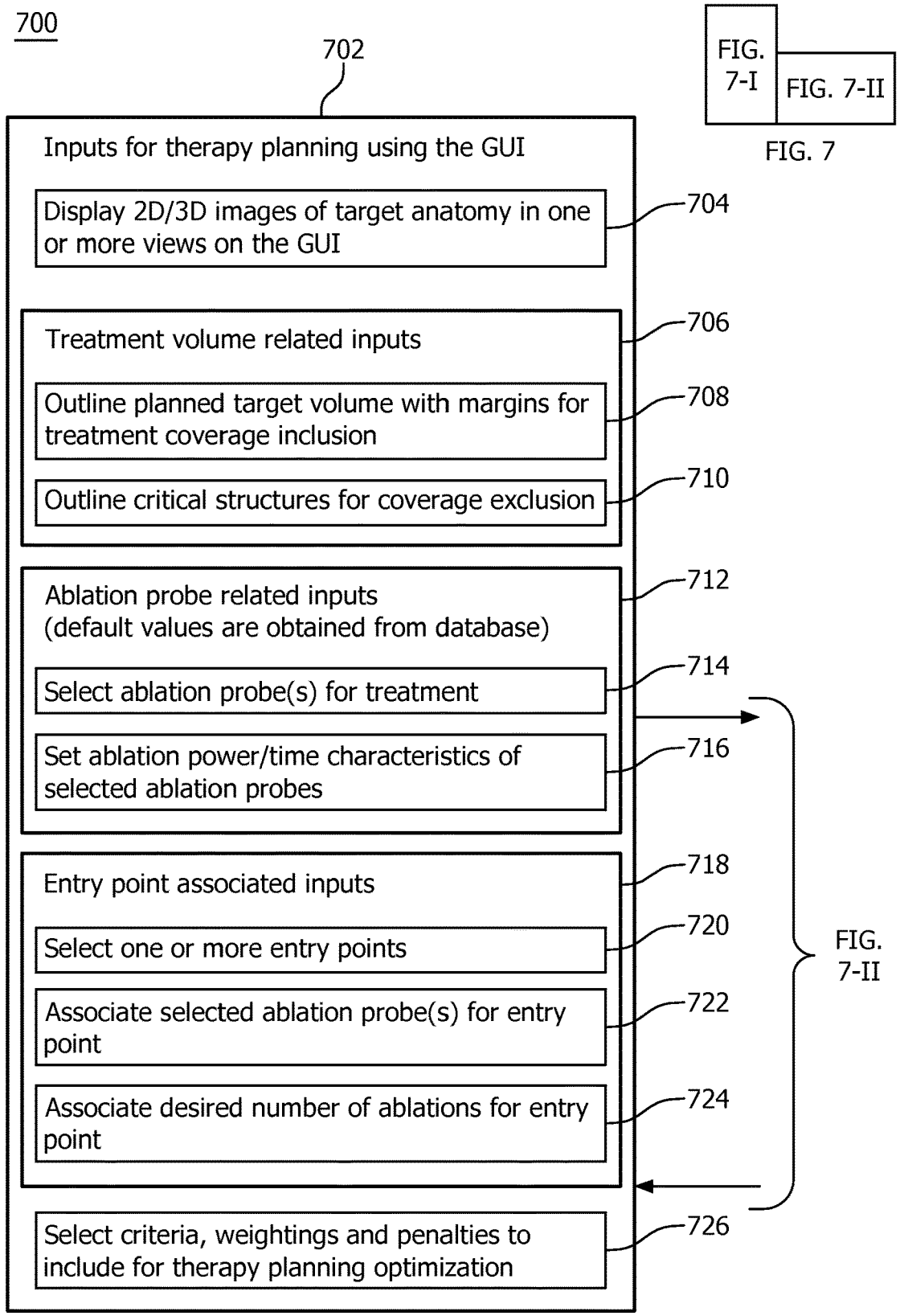
FIG. 7-I

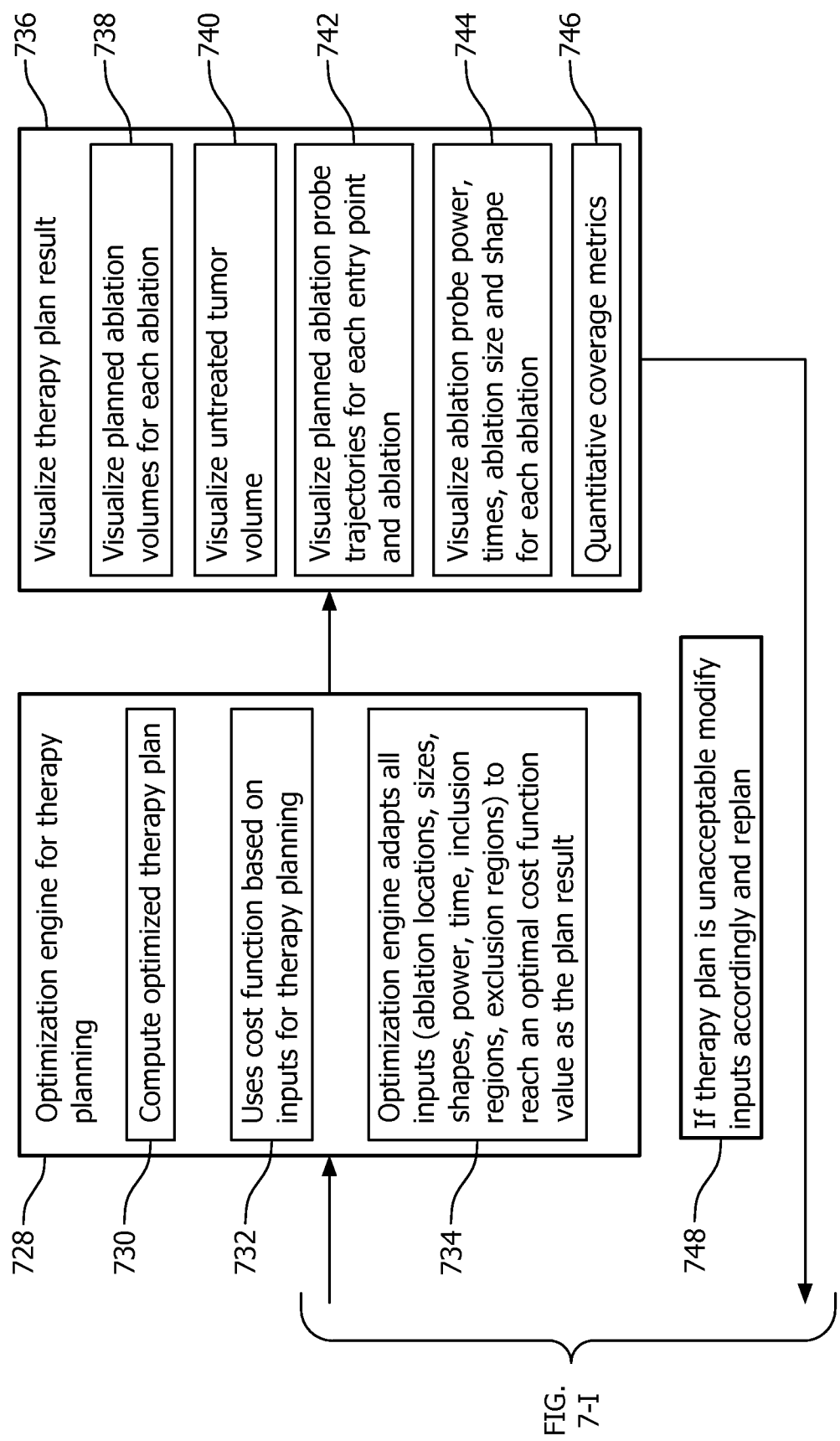

ABLATION PLANNING SYSTEM

CROSS-REFERENCE TO PRIOR APPLICATIONS

This application is the U.S. National Phase application under 35 U.S.C. § 371 of International Application Serial No. PCT/IB2012/053860, filed on Jul. 27, 2012, which claims the benefit of U.S. Provisional Applications Ser. Nos. 61/566,630, filed on Feb. 3, 2012; 61/514,914, filed on Aug. 4, 2011; and 61/512,510, filed on Jul. 28, 2011. These applications are hereby incorporated by reference herein.

This application claims priority to commonly assigned provisional application Ser. No. 61/512,510, filed Jul. 28, 2011, and commonly assigned provisional application Ser. No. 61/514,914, filed Aug. 4, 2011, both incorporated herein by reference.

This disclosure relates to medical treatment systems and methods, and more particularly to ablation planning systems and methods for patient treatment with improved accuracy.

Microwave ablation (MWA) is a minimally invasive procedure used for the treatment of localized tumors most commonly in the liver, kidney and lung. For large or irregularly shaped lesions, the treatment requires more than one session, and the physician has to plan in advance where to place the needle and how many ablations are needed. MWA has become a recommended treatment modality for interventional cancer treatment, and has received increasing attention in recent years. Compared with radiofrequency ablation (RFA), MWA provides more rapid and larger-volume tissue heating, and multiple antennae can be used simultaneously with synergistic effects, e.g., the ablation volume may be increased beyond that achievable with several sequential single-probe ablations. In addition, MWA is less susceptible to decreased ablation volumes due to the heat sink effect (e.g., cooling provided by blood vessels adjacent to the tumor volume).

Mental planning of ablations is a daunting task. Physicians have to picture complete coverage of a three dimensional tumor volume using overlapping ellipsoidal ablation volumes in different orientations. Insufficient and imprecise planning leads to incomplete treatment and potential recurrence of cancer or other effects. Conventionally, a single ablation probe inserted through a single entry point is preferred to minimize trauma. However, if multiple probes are clinically available, large or irregularly shaped lesions could be treated more effectively than with conventional single probe units, thus potentially decreasing procedure time and complications. Mental planning can be an even more daunting task with multiple entry points. Physicians have to picture and plan how to completely cover a three dimensional tumor using an overlapping ellipsoidal ablation volume from different orientations. Insufficient and imprecise planning leads to incomplete treatment and potential recurrence of cancer.

In accordance with the present principles, an ablation planning system includes a user interface configured to permit selection of inputs for planning an ablation procedure. The user interface is further configured to incorporate selection of ablation probes and one or more combinations of ablation powers, durations or parameters applicable to selected probes in the inputs to size the ablation volumes. The user interface includes a display for rendering internal images of a patient, the display permitting visualizations of the ablation volumes for different entry points on the internal images. An optimization engine is coupled to the user interface to receive the inputs and is configured to output an optimized therapy plan which includes spatial ablation locations and temporal information for ablation so that collateral damage is reduced, coverage area is maximized and critical structures are avoided in a planned target volume.

An ablation planning system includes a user interface configured to permit selection of inputs for planning an ablation procedure, the user interface further being configured to incorporate ablation durations in the inputs to size the ablation volumes. The user interface includes a display for rendering internal images of a patient. The display permits visualizations of the ablation volumes for different entry points on the internal images, and the display is configured to render internal images of a patient and provide selection controls to enable a user to select an internal image and a view of the internal image. A database is configured to store the internal images and information on the ablation probes to assist in determining sizes and shapes for the ablation volumes for a given planned target volume by associating power and time characteristics with the sizes and shapes of the ablation volumes. An optimization engine is coupled to the user interface to receive the inputs and is configured to output an optimized therapy plan which includes spatial ablation locations and temporal information for minimally needed ablation durations, so that collateral damage is reduced, coverage area is maximized and critical structures are avoided in a planned target volume.

A method for planning an ablation procedure includes displaying an internal image of a patient on a display of a user interface; selecting an ablation probe or set of probes for performing an ablation procedure using the user interface; selecting a point or points of entry for the ablation probe or set of probes on the internal image; inputting information to an optimization engine for a set of inputs including the ablation probe or set of probes selected, the point or points of entry selected, time and power information to determine sizes and shapes of ablation volumes; and outputting from the optimization engine an optimized therapy plan based on reducing collateral damage, maximizing coverage area and avoiding critical structures in a planned target volume.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein:

FIG. 7 is a block/flow diagram showing steps for planning, executing or training for an ablation procedure using the system of FIG. 6 in accordance with another illustrative embodiment.

Figure 1:
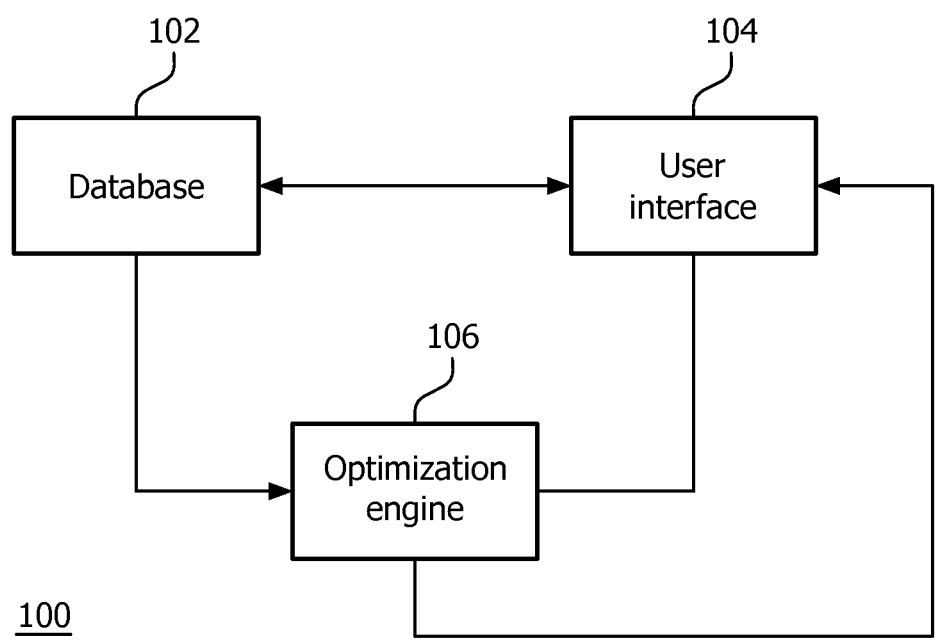
FIG. 1 is a block diagram showing a high-level embodiment of an ablation therapy system in accordance with the present principles.

In accordance with the present principles, to generate a clinically relevant and reliable result, an automated planning system is provided that warrants precise locations of probes and complete coverage of tumor and margin (planned target volume, PTV). An automatic coverage method is described. The searching for the best ablation centers is treated as an iterative non-linear optimization problem where a cost function is formulated as the weighted sum of un-ablated PTV volume and unwanted collateral damage to the adjacent health tissue. This is a non-linear optimization problem which aims to minimize cancerous tissue that is untreated and the healthy tissue that is damaged. The entire planning system is implemented with a Graphic User Interface (GUI) that allows for interactive planning scenarios including proper probe selection, skin entry localization, ablation number specifications, etc. The planning system is integrated as a first step of an electromagnetically guided navigation system where planning is executed to permit plans to be transferred to subsequent navigation working steps in an adaptive manner.

Focal tumor ablation is an effective alternative to surgical resection. A microwave ablation (MWA) planning system in accordance with one embodiment includes a database, an optimization engine and a user-interface. The system provides optimized ablation parameters as output to help physicians maximize tumor coverage, minimize collateral damage to healthy tissue and/or optimize overall procedure execution in other ways, such as by avoiding critical structures, such as blood vessels or the like. The system's user-interface component advantageously provides input/output specific to microwave ablation, but is also applicable to other ablation systems that have similar information needs (e.g., cryogenic ablation). Such a planning system can assist interventionists to best plan the ablation procedure using resource information available from the database and information specified by the users as input. The output of the system includes but is not limited to the optimized ablation parameters computed by the optimization engine.

To facilitate efficient and accurate execution of ablation procedures, ablation planning systems have addressed the needs for radio frequency ablation (RFA) procedures. Such planning systems generally determine the number and/or location of individual ablations that together allow complete and efficient eradication of a tumor. These planning systems, however, do not exploit the specific advantages of MWA technology which may include, e.g.: 1) The ability to customize an ablation size by choosing specific power/time/temperature parameters when running the MWA device; and 2) The ability to insert several probes simultaneously with synergistic effects, thus increasing the ablated volume further and decreasing procedure time. As a result of the more rapid destruction of tissue, MWA procedures are generally more difficult to control than RFA and may cause harm if not used with care and confidence. A planning system in accordance with the present embodiments addresses MWA-specific parameters and workflows and is highly desirable to help physicians achieve better microwave ablation results.

In contrast to RFA, MWA probes can produce ablations in a range of ablation sizes. The size of the ablation zone is a function of time and power supplied to the probe. Planning systems geared towards RFA make no recommendation for specific power/time settings, nor are they able to take advantage of the variable ablation sizes in determining the optimal ablation plan. Furthermore, there may be patient-specific considerations (or computational complexity and time constraints) that would limit the choices of power/time settings that the physician is willing to consider. There may also be patient-specific considerations or overall time/throughput considerations that would make a particular treatment approach with multiple simultaneous probe insertions advantageous.

MWA manufacturers may provide only limited information on ablation volume varied with power/time, and if provided, the ablation information only includes discrete power/time inputs and their corresponding ablation sizes (e.g., ablation size at 5 minutes, 10 minutes, using power 50 W). It is difficult for users to extrapolate the size of a necrosis zone using discrete intervals of the given inputs (e.g., ablation zone at 8 minutes). The present embodiments address these shortcomings and clinical needs of the prior art by providing a microwave ablation planning system with a user interface, optimization engine, and other components that permit efficient planning and execution of microwave ablation procedures.

It should be understood that the present invention will be described in terms of microwave ablation; however, other ablation technologies are contemplated. In particular, the present principles are particularly useful with ablation technologies that employ time dependent variations for ablation zones. In other embodiments, in addition to or instead of time dependent ablation treatment volumes, other dependent variables may be employed, such as, temperature-dependent variables, power-dependent variables, etc.

It also should be understood that the present invention will be described in terms of medical instruments; however, the teachings of the present invention are much broader and are applicable to any instruments employed in treating or analyzing complex biological or mechanical systems. In particular, the present principles are applicable to internal tracking and planning procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), DVD and Blu-Ray™.

Referring now to the drawings in which like numerals represent the same or similar elements and initially to FIG. 1, a high level block diagram shows a planning system 100 in accordance with one illustrative embodiment. The planning system 100 assists doctors, technicians, etc. in generating a plan on how to ablate a tumor or other tissue, visualize the ablation plan and evaluate quantitative metrics associated with the plan. A database or memory system 102 includes storage for information on a set of ablation probes and their properties, e.g., power and/or time data versus ablated volume, ablation shape/size characteristics, etc. This information is made available to a user from the database 102 at a user-interface 104. It should be understood that an ablation probe can be used interchangeably with ablation needle, ablation antenna, ablation applicator, etc. An optimization engine 106 optimizes an ablation plan and can read the probe properties of selected probes from the database 102. The optimization engine 106 also considers user inputs, e.g., selected probe, tumor segmentation, skin entry points, number of ablations, time/power preferences, etc. The optimization engine 106 uses the inputs to create and communicate the ablation plan to the user-interface for visualization and modification.

In one embodiment, the planning system 100 includes a microwave ablation (MWA) planning system. The system 100 addresses MWA-specific parameters (variable ablation sizes as a function of power, time and temperature) and workflows that help physicians achieve better microwave ablation results.

The ablation probe database 102 includes all relevant properties for different ablation probes, for example, size of the ablation zone as a function of different times, power settings for a given probe, etc. The database 102 provides resource information of ablation probes and also allows users to refine the probe properties through the user interface 104. The user interface 104 permits user input and selection of all parameters relevant for optimizing the ablation plan, and display (and select) results and choices that become the output of the plan computation. The inputs may include, e.g., tumor segmentation, one or more skin entry points, number of ablations either in total or by number of ablations from each entry point, selection of one or more ablation probes applicable to all entry points or to specific entry point(s), a subset of power/time settings to be considered for a given ablation probe, etc. The displayed plan outputs may include, e.g., number and location of ablations, shape/sizes and power/time settings of each ablation, etc. User choices based on plan output may include, e.g., choosing one of several possible power/time settings to achieve the planned shape/size of a given ablation.

The optimization engine 106 optimizes a treatment plan and may be employed to monitor activities to make suggestions for future actions based upon the execution of previous events. The user-interface 104 interacts with the ablation probe database 102 and passes parameters to the optimization engine 106. The parameters include, for example, a user-specified set of ablation probes and a user-specified set of power-time characteristics to be used with those ablation probes. The optimization engine 106 computes an ablation plan based on the inputs from the user interface 104, and the resource information from the ablation probe database 102. The optimization engine 106 passes the ablation plan results back to the user interface 104 for display and, optionally, additional user choices as input. The ablation plan may be tailored to achieve a number of objectives, e.g., maximize tumor coverage, minimize number of ablations, minimize time of ablations, minimize collateral damage, etc. The optimization engine 106 is however not restricted to these objectives.

In one embodiment, a search for the best ablation coverage can be seen as an iterative optimization problem. The ablation centers are steered toward the location which minimizes both un-ablated planned target volume (PTV) (tumor tissue that ought to be ablated but is not yet ablated) and collateral damage caused to healthy tissue. The optimization problem can thus be presented as:

$$\hat{\Theta} = \operatorname*{argmin}_{\Theta} C\left(V_{PTV}, \sum_i V_{Ai}(\Theta_i, e_i)\right) \quad (1)$$

where $V_{PTV}$ is the planned target volume (PTV) and $V_{Ai}$ is the $i^{th}$ ablation volume characterized by the parameter set $\Theta_i$ at given skin entry point $e_i$. C is the cost function. $\Theta_i$ is a four dimensional (4D) parameter defined as:

$$\Theta_i = [t_x, t_y, t_z, s]^T \quad (2).$$

The ablation center (the center of the ellipsoidal ablation model) is denoted as $t_x$, $t_y$, $t_z$ in three dimensions. s is a scale factor between 0 and 1 that parameterizes the radii from minimum to maximum.

Unlike RF ablation where the power and time are fixed and the ablation size is invariant, microwave ablation manufacturers may provide an array of ablation sizes and their respective power/time settings. A model in accordance with the present principles interpolates microwave ablation radii from available discrete power/time inputs, assuming radii grow proportionally with increasing time and increasing power. Other relationships are also contemplated.

An iterative search problem may be implemented using, e.g., optimization techniques to minimize the following illustrative cost function C:

$$C = V_{PTV} \cap (\overline{\cup V_{Ai}}) \cdot \mu_u + \overline{V_{PTV}} \cap (\cup V_{Ai}) \cdot \mu_c + \varphi \cdot \mu_p \quad (3)$$

where $V_{PTV}$ is the PTV volume, $V_{Ai}$ is the $i^{th}$ ablation volume, $\mu_u$ and $\mu_c$ are the weighting factors for unablated PTV and collateral damage, respectively. The symbol $\cap$ between two volumes represents the count of voxels that are set in both volumes (intersection of the two volumes), whereas the symbol ∪ represents the count of voxels that are set in either volume (union of the two volumes). The horizontal bar above the two volumes, $V_{PTV}$ and the union of all the ablation volumes $\cup V_{Ai}$ in the cost function expression, represent the inverse of the volumes, i.e., voxels that are "excluded" from the respective volumes. The cost function is normalized based on these weights which reflect user preferences in penalizing unwanted results.

In case of some undesirable situations, a penalty function φ will be introduced. For example, for simultaneous ablation, a requirement may be provided that adjacent ablations performed simultaneously are to be kept a minimum distance apart to ensure that the ablation process is performed optimally. The penalty function φ is then defined as a function of the distance between adjacent ablation centers. We add a penalty to the cost function using the third expression $\mu_p \cdot \varphi$ to ensure the adjacent needle ablation centers are not too close. Another example of a penalty function is when a critical structure is present close to the PTV. The method may penalize the situation where the ablation volume overlaps with the critical structure. The method will successively iterate until convergence, and an optimum solution for Eq. (1) is achieved. During this process, the $V_{PTV}$ (PTV volume) is constant, $V_{Ai}$ (ith ablation volume) is changed with positive or negative perturbations of four independent parameters from set $\Theta_i$. The probe is permitted to be repositioned after the first session for sequential ablation sessions. For single-entry ablation, the probe is allowed to move anywhere within the PTV (unconstrained search); while for multi-entry ablation, the probe is allowed to move along the trajectory between entry point and ablation center (constraint trajectory search). For example, in sequential multi-ablation sessions, the probe can be repositioned after each ablation in an unconstrained way. When using multiple skin entry points for simultaneous ablations, the probes are only allowed to move along the trajectory between entry point and ablation center (constraint trajectory search), in accordance with how ablations are executed in clinical practice.

For modeling synergetic effects using simultaneous MWA applicators, the cost function C could be adjusted such that when the needles are mostly parallel, the synergetic ablation volume which is supposed to be larger than the summation of individual ablations could be extrapolated from the manufacturer's data brochure. The optimization engine 106 considers the objectives that provide parallel needles to create a larger ablation zone. In another embodiment, ablation sizes could be modeled using principals of thermal physics including, e.g., tissue properties, thermal coefficients will be integrated into the model and employed to estimate ablation regions using power and time data.

Figure 2:
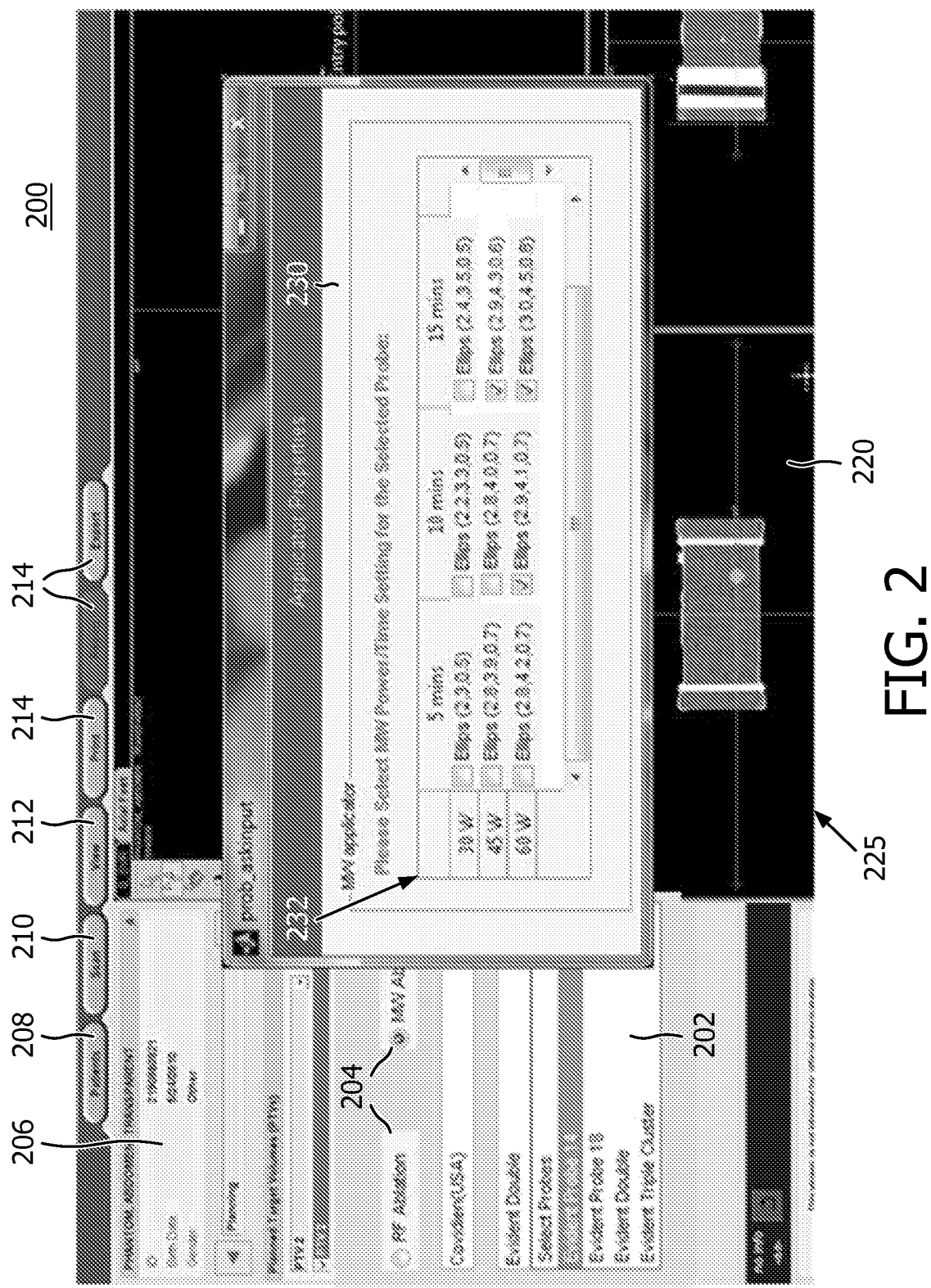
FIG. 2 is a diagram showing an illustrative graphical user interface for planning an ablation procedure in accordance with one illustrative embodiment.

Referring to FIG. 2, a planning tool or ablation treatment planning system 200 includes a graphical user interface of the user-interface 104 for therapy planning. The ablation treatment planning system and coverage algorithm 200 provide image manipulation of pre-operative CT images 220. Quick 3D automatic or semi-automatic (involving some user interaction) segmentation of tumors can be performed, and once a tumor is segmented, a margin which typically ranges from 5-10 mm can be conveniently added to decide the planned target volume (PTV). The user is then asked to pick the preferred ablation needle and one or more preferred needle entry points on the patient's skin. Based on manufacturers' data brochures and published literature on animal/patient trials using these probes, an ablation template can be modeled as either a spherical or ellipsoidal three dimensional object with three known radii. The method can be easily extended to other geometrical shapes if necessary.

In one embodiment, the system 100 prompts users to select an ablation probe from an ablation probe menu or pane 202 and specify a preferred power and time combination(s) to be considered for the given ablation probe in an applicator properties sub-screen 230 that pops up when the probe or applicator is selected in the pane 202. The sub-screen 230 may include a power/time table 232 listing in a matrix of powers and times and their resulting ablated volume. For each power/time setting, the table 232 provides information about a size of the ablation volume modeled as an ellipsoid-shape 3D structure with three distinctive radii in three dimensions (e.g., Ellips (2,3,0.5). Other shapes may also be employed. The user may select the modeled shape that is desired and apply the shape at a particular location in an image screen 225. These user inputs may be based on user experience and understanding of the patients' anatomy, and help to confine the search space for the optimization engine 106.

The tool 200 may be employed to chart out or plan a complete procedure, selecting different probes, different shapes, different power/times, etc. The planning tool 200 may include user-selected functions to permit planning using different technology, e.g., by selecting one of fields 204 (RFA or MWA). Other technologies may be added as well. Such technologies would include at least time/power dependent ablation volume shapes to provide a highly customizable and flexible ablation plan. The user may select different patients 208, different scans 210, different views 212, etc. from a memory or database storing these items. A description pane 206 may be provided, which includes data on the images, views, patients, etc. Other useful functions 214 may also be provided, such as export a plan, print, report, zoom, etc.

Figure 3:
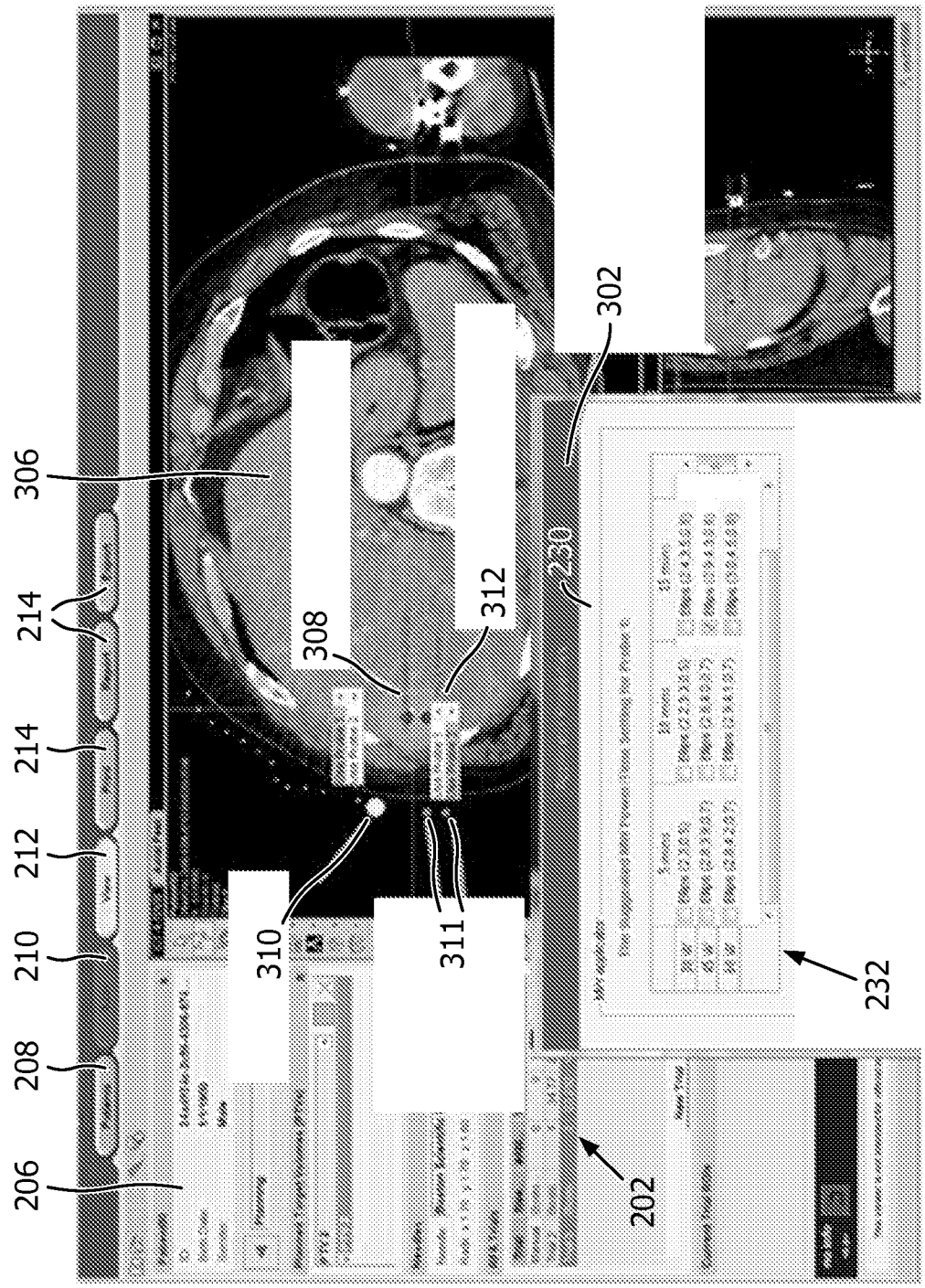
FIG. 3 is another diagram showing the illustrative graphical user interface of FIG. 2 showing image details for planning the ablation procedure in accordance with the illustrative embodiment.

Referring to FIG. 3, a user-interface instance 300 of the microwave ablation planning system 200 is illustratively shown in accordance with one embodiment. The instance 300 illustratively includes an image 302, e.g., a computed tomography scan, magnetic resonance image, etc. In this example, the image 302 includes a section 306 of a liver with a segmented tumor 308. Skin entry points 310, 311 are specified by the user. For each skin entry point 310, 311, an ablation probe is selected with preferred power/time settings from the menu/table 232 in pane 230. The optimization engine 106 provides an ablation plan that includes planned ablation volumes 312 with the recommended microwave ablation time and power settings based on pre-defined optimization objectives. The skin entry points 311 are for parallel needles, which may be employed to reduce overall ablation time, as one alternative.

Using the selected entry point(s) 310 or 311 on the skin, a single ellipsoidal ablation is overlaid on the PTV to aid in understanding the size of an ablation. It would be difficult for a radiologist to arrive at an estimate for the number of ablations needed to cover this complex, highly irregular-shaped PTV with the given ablation shape. The present embodiments compute solutions based on different entry points and result in overlapping spherical/ellipsoidal ablations that optimally cover the PTV with minimal collateral damage. With the aid of visualization, the radiologist can determine if the number of ablations and the collateral damage are acceptable. Since the computation is quick, it is easy to modify the entry point or needle to create an alternative plan. Also, the estimation of tumor coverage is done in a fully automatic fashion.

Figure 4:
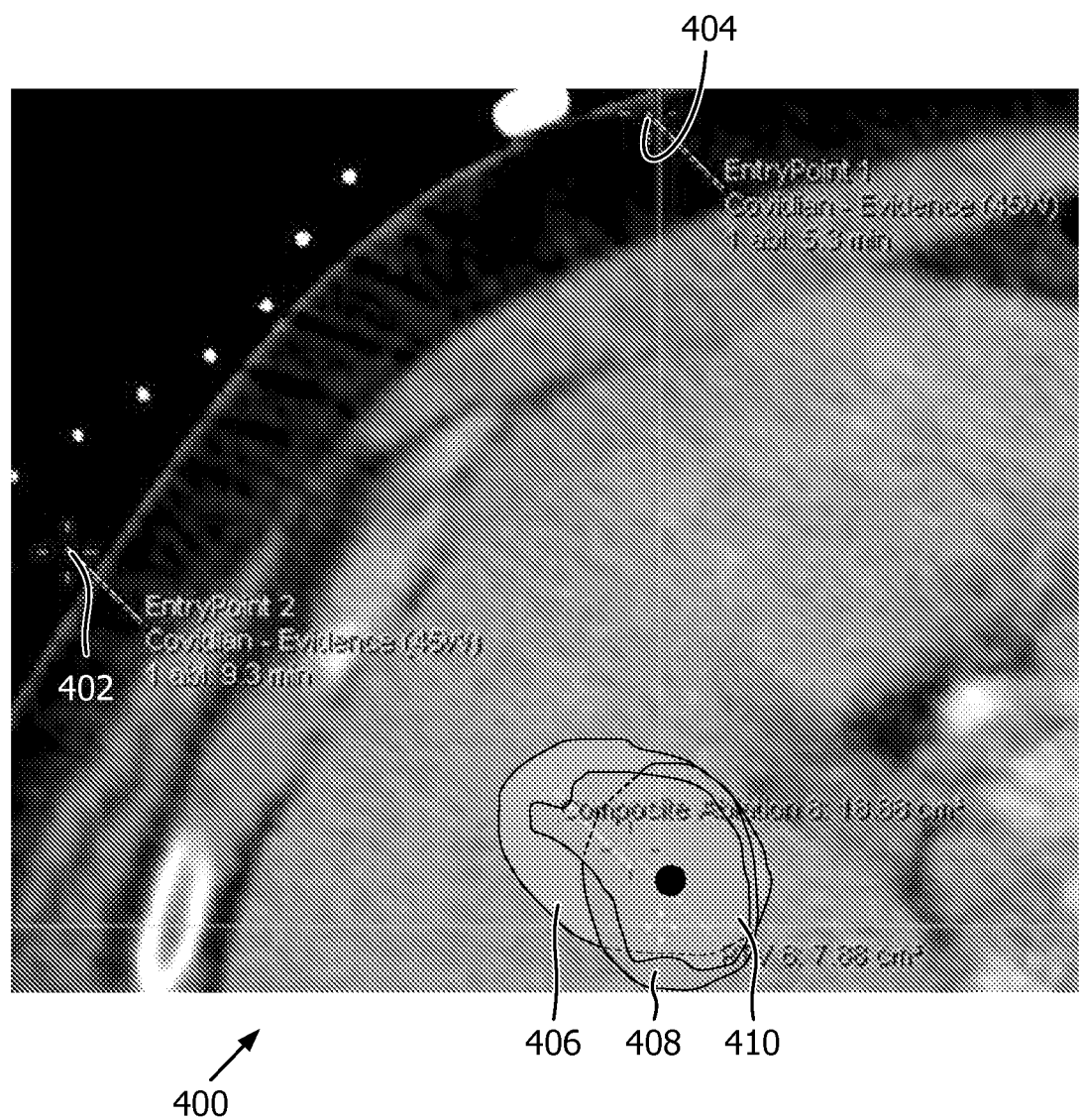
FIG. 4 is another diagram showing greater detail on an image for planning the ablation procedure in accordance with the illustrative embodiment.

Referring to FIG. 4, an image 400 is illustratively shown to demonstrate some of the features in accordance with the present principles. Image 400 includes a scan section having an irregularly shaped tumor 410. Entry point-1 404 is shown for providing a planned ablation volume 408, and entry point-2 402 is shown for providing a planned ablation volume 406. The highly irregular tumor 410 is covered by a PTV which includes two ablations (406 and 408) using a Covidian-Evidence™ MWA probe at 45 W. An estimated percentage of PTV coverage is 99.86% with 11.13 cm³ of collateral damage in this case. As the output of the algorithm, ablation 408 from the entry point-1 404 is suggested to ablate for 5.3 minutes, whereas the ablation 408 from entry point-2 402 is suggested to ablate for 9.3 minutes.

Referring again to FIG. 1 with continued reference to FIGS. 2-4, the system 100 prompts the user to provide the preferred power/time setting for the selected probes and user-selected entry points. The optimization engine 106 provides an ablation plan with a list of power and time combinations that could be employed for the selected ablation probe(s), to satisfy pre-defined optimization objectives, e.g., maximize tumor coverage, minimize number of ablations, minimize time of ablations, minimize collateral damage, etc. The optimization engine 106 may also consider alternative entry points, ablation times, probes, etc. to better achieve these objectives.

The planning system's input can take a variety of forms in terms of components to be visualized and presentation style. For example, user input could include one or more of these components: tumor segmentation, one or more skin entry points, number of ablations either in total or by number of ablations from each entry point, selection of one or more ablation probes, a subset of power/time settings to be considered for a given ablation probe, inter-probe distance (applicable to parallel probe insertions), etc. The user input could be presented in one of multiple graphical user interface forms e.g.: table, checklist, spreadsheet, drop-down menu, information window which provides drawing and annotation of ablation zone in 2D or 3D for a given ablation setting, etc. The selection of one or more ablation probes may be performed manually or automatically. For example, ablation probe types could be manually specified by user-input, or they could be pre-selected in the user-interface via an automatic detection of probes connected to the system.

The planning system's output can also take a variety of forms in terms of components to be visualized and presentation style. The planning system's output may include one or more of a recommended power and time for any selected probe, shape/sizes of each ablation, recommended entry point locations, recommended probe types, a recommended number of ablations to be considered for each skin entry point, etc. The planning system's output could be presented in one of multiple graphical user interface forms, such as, e.g., a table, a highlighted list, a marked spreadsheet, a display and/or an overlay of estimated ablation zone/parameters onto the original images (e.g., CT) with power/time suggestions, metrics of tumor coverage (percentage of tumor coverage, collateral damage), etc.

In one embodiment, outputs (e.g., power and time for a given probe) can be a subset of the input selections. Output of the system may also include error/warning messages. The system could flag a warning message, indicating the user selection is not appropriate given the patient anatomy and the tumor size/geometry, etc. In one example, the selected power and time settings may not be able to cover the entirety of the tumor. If necessary, the user can choose to override the recommended settings by discarding the current plan and running a new instance of the plan using new combinations of inputs. Where the planning system 100 provides an output that includes recommended ablation probe types and power/time settings for the recommended probes, the system 100 may also be used for other parameter optimization. For example, in one embodiment, if the users have only a small selection of ablation probes, the system could specify which probe should be chosen to treat this specific patient, as a result of the estimation from optimization engine 106. In another embodiment, the system 100 could specify which skin entry points are beneficial for use in the procedure based on the objectives included in the optimization engine 106.

Preferred embodiments are applied to image-guided microwave ablation; however, other ablation systems may be employed, especially where there is high dimensional parameter space for each insertion and ablation. For example, for other ablation modalities (e.g., HIFU, Cryo) where variable ablation sizes also vary with specific input parameters, these parameters can be specified by the users as the input for the planning system 100, and optimized through the optimization engine 106, resulting in the output for optimized parameters. Unlike RF ablation where the power and time is fixed and the ablation size is invariant, microwave ablation provides an array of time and power settings, and can vary in their respective ablation sizes as needed. For a given power, a model can interpolate microwave ablation radii from a shortest time to a longest time, assuming three radii grow proportionally with time. In this way, ablation shapes and sizes may be determined and implemented using a specific time and power combination. Given the size and shape needed for an ablation can be provided by applying an appropriate time of ablation.

To assess the accuracy of the planning methods disclosed, the present inventors created, on pre-operative CT images, a series of lesions with known geometries, i.e., spherical and ellipsoidal PTVs are synthesized to serve as the ground truth. Estimated ablation centers, if planned properly, should coincide with the center of the geometry of these spheres/ellipsoids. In addition, the estimated ablation radii should circumscribe the boundary of the PTV with minimal damage to the healthy tissue. Among thirty runs on three known geometry centers (one sphere, two ellipsoids), the Mean Location Distance Error (MLDE) which is obtained by comparing the computed ablation center with the ground truth ablation center achieves 0.66 mm (STD: 0.22 mm). The Mean Radii Distance Error (MRDE) which is estimated by comparing the computed ablation radii with the ground truth radii reaches 0.53 mm (STD: 0.23 mm). These preliminary and illustrative results demonstrate the accuracy and robustness of the described embodiments. Table 1 shows comparison results for the simulations to demonstrate the accuracy and feasibility of the disclosed methods

TABLE 1

MLDE (mm) and MRDE (mm) are estimated based on the comparison with the ground truth after ten runs of the optimization algorithm. Three known geometries on two PTVs are used for this testing.

| | MLDE_x (mm) | MLDE_y (mm) | MLDE_z (mm) | MLDE (mm) | MRDE_r (mm) |
|---|---|---|---|---|---|
| PTV1 : one ablation | 0.71 ± 0.43 | 0.41 ± 0.07 | 0.87 ± 0.07 | 0.66 ± 0.14 | 0.21 ± 0.07 |
| PTV2: $1^{st}$ ablation | 1.06 ± 0.59 | 1.42 ± 0.83 | 0.34 ± 0.25 | 0.94 ± 0.44 | 0.99 ± 0.54 |
| PTV2: $2^{nd}$ ablation | 0.76 ± 0.13 | 0.11 ± 0.09 | 0.24 ± 0.16 | 0.38 ± 0.07 | 0.41 ± 0.08 |
| Mean | 0.85 ± 0.38 | 0.65 ± 0.33 | 0.48 ± 0.16 | 0.66 ± 0.22 | 0.53 ± 0.23 |

Figure 5:
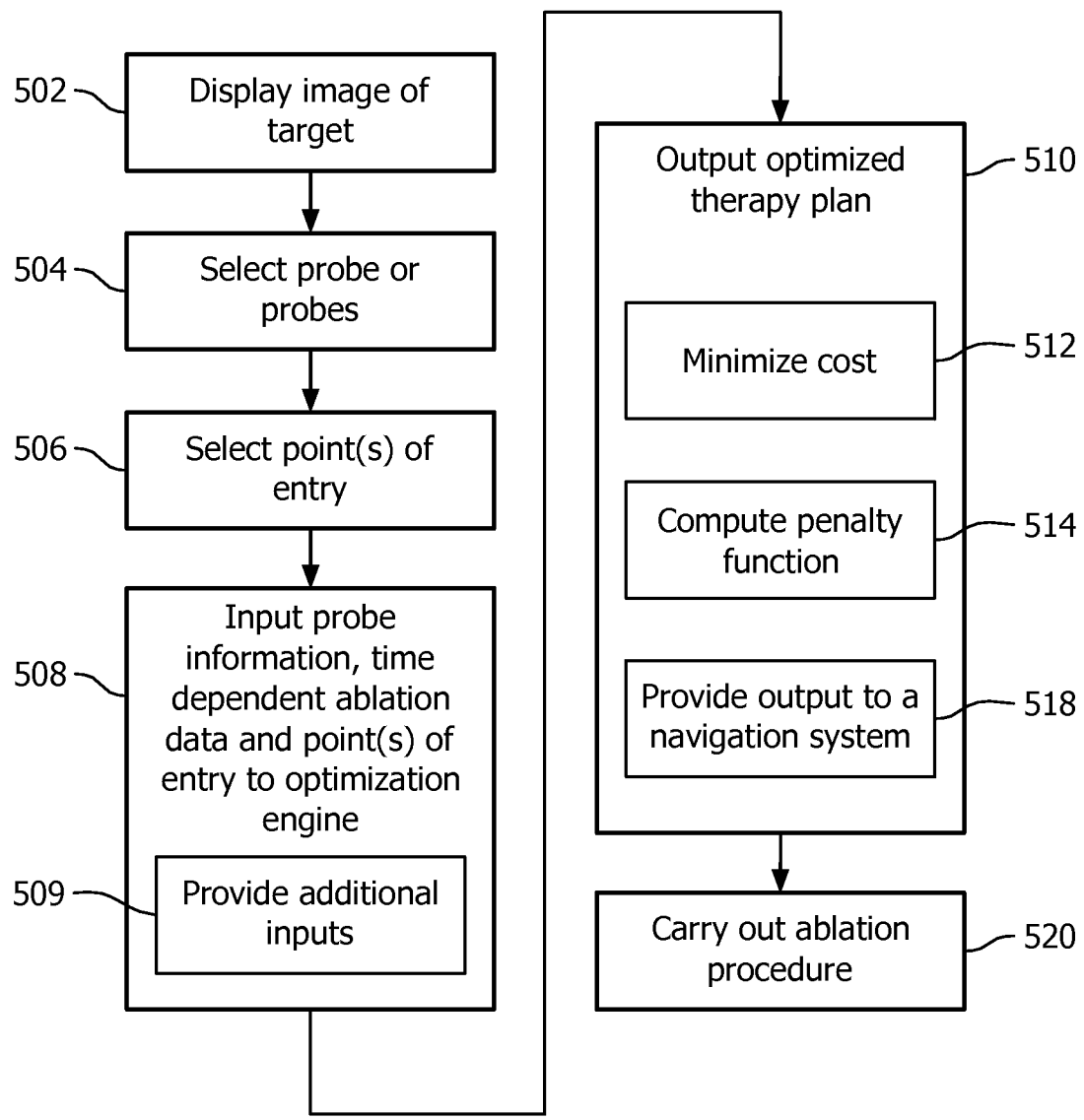
FIG. 5 is a block/flow diagram showing steps for planning, executing or training for an ablation procedure in accordance with an illustrative embodiment.

Referring to FIG. 5, a method for planning an ablation procedure is depicted in accordance with illustrative embodiments. In block 502, an internal image of a patient on a display of a user interface may be displayed. The image may be a pre-operative image, a rendering of an image or a model employed for simulation or practice. The image may be a 2D image or a 3D image and may include multiple views that can be controlled using the user interface. In block 504, an ablation probe or set of probes for performing an ablation procedure using the user interface is/are selected. The ablation probe may include a microwave ablation probe, and the information preferably includes power and time data for a plurality of ablation shapes. The shapes may include spherical or ellipsoidal shapes, although other shapes may be employed as well. In block 506, a point or points of entry for the ablation probe or set of probes is/are selected on the internal image. Other input information may also be selected or provided by a user. In this way, the experience of the user and the convenience and power of a computer system can be combined to provide a synergistic and powerful planning tool. In block 508, information about the ablation probe or set of probes and the point or points of entry are input to an optimization engine. Time and power is included in the input information to determine sizes and shapes of ablation volumes. The time and power are provided for time dependent ablation volumes, e.g., the ablation volume is proportional to the time/ablation duration. Other information may also be included in the input. In block 509, the set of inputs may include one or more of a type of ablation probe, a margin of error, ablation coverage, collateral damage, ablation time, etc.

In block 510, an optimized therapy plan is output from an optimization engine based on, e.g., reducing collateral damage and maximizing coverage area in a planned target volume. Other criteria may be set as well instead of and/or in addition to the damage and coverage criteria. In block 512, the optimization of the therapy plan may include minimizing a cost based on a set of inputs. The inputs may include at least the point or points of entry and the information on the ablation probe or set of probes. In block 514, cost minimization may include computing a penalty function to penalize the cost for an unwanted effect. The penalty function may be tailored to account for one or more effects, such as employing multiple probes, ablation sites that are too close, anatomical features that are nearby, etc. The cost function and penalty function may be altered in real-time at the user interface by selecting different scenarios or physiological conditions in a patient, e.g., entering blood flow conditions for a nearby blood vessel, accounting for scar tissue, entering physical properties measured for a specific patient, etc. The optimized therapy plan may include one or more types of ablation probes, locations of entry points, a number of ablation probes used, locations for a minimum number of ablations, ablation locations to minimize collateral damage, a minimized ablation time, etc. In block 518, the recommendations and/or outputs may be automatically input to a navigation system to carry out the therapy plan. In block 520, the system may be employed in providing an interface for carrying out an ablation therapy procedure (or providing training).

Figure 6:
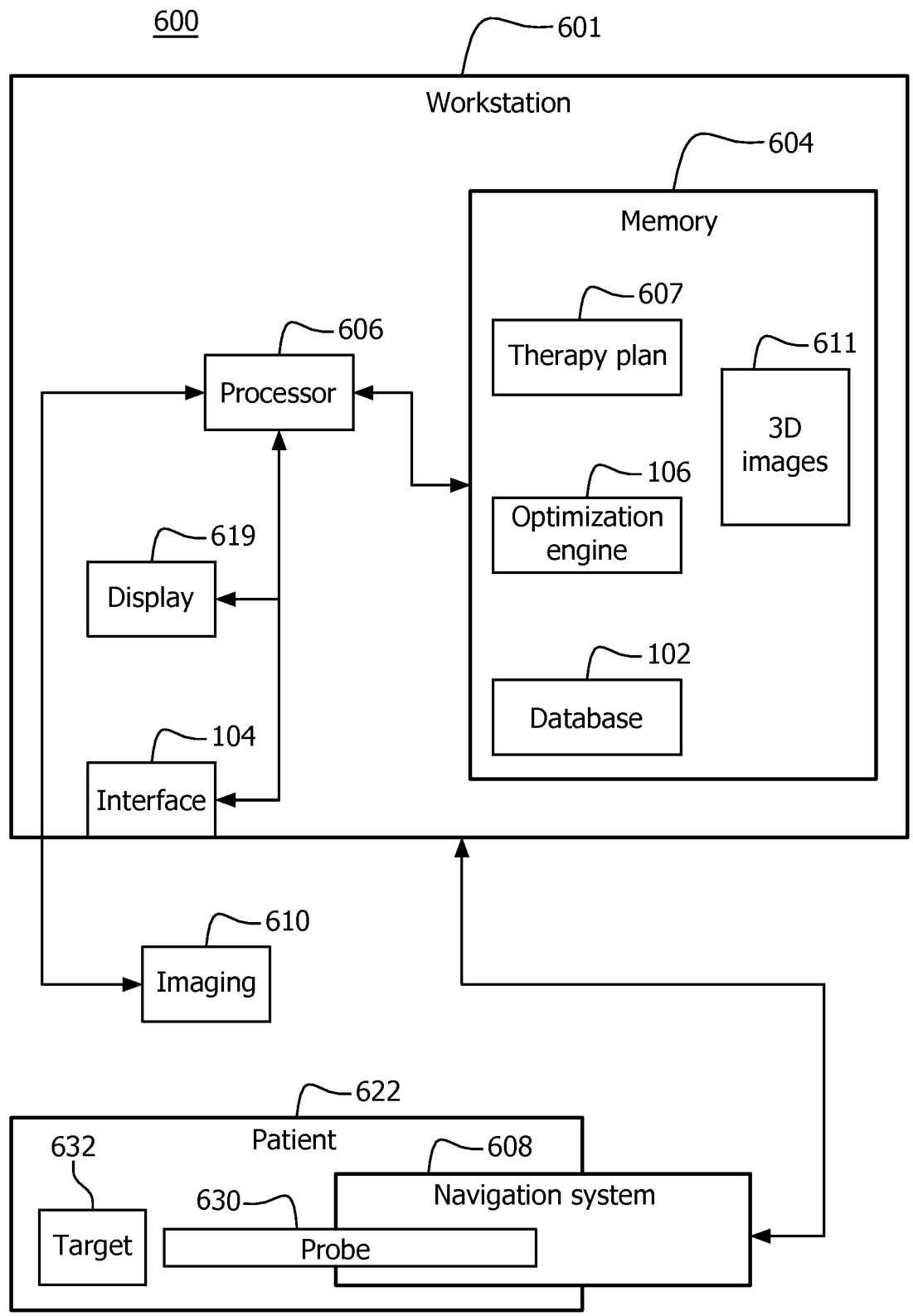
FIG. 6 is a block diagram showing a system for planning and performing an ablation procedure in accordance with the present principles.

Referring to FIG. 6, a treatment system 600 for ablation therapy is shown in accordance with one illustrative embodiment. System 600 may be part of a therapy planning and procedure monitoring workstation 601 that links optimized plan information, tissue interaction modeling, dose monitoring, and clinical outcomes data based on a patient-specific basis for procedure optimization, reporting, and physician training System 600 may include memory storage 604. The database 604 stores images 611, preferably three-dimensional (3D) images, of a patient 622 on which a procedure is to be performed. Workstation 601 includes a processor 606 capable of execution of an optimized therapy plan 607 stored in memory 604.

An ablation probe navigation system 608 is preferably controlled by and provides data to the computer 606. The procedure may be conducted manually as well, without the navigation system 608. The navigation system 608 receives spatial information, commands from the workstation 601 and carries out the plan 607 created by the planning system 100. The workstation 601 and the planning system 100 may be integrated together or may be separate units.

An ablation probe or a set of probes 630 are selected and coupled to the system 600. In one embodiment, the database 102 and optimization engine 106 are stored in memory 604. The probe information may be referenced from the memory 604 to obtain the information needed for planning the therapy. In another embodiment, by connecting the probe or probes 630 to the system 600, the system senses the types of probes and looks up the probe data from memory 604. Feedback from the ablations on a target 632 in accordance with the plan 607 may be collected by sensors or by an imaging system 610, which may include fluoroscopy, ultrasound, etc. The feedback may include PTV coverage area, measured temperatures, etc.

Programming, device control, monitoring of functions and/or any other interactions with the workstation 601 may be performed using the user interface 104. A display 619 may also permit a user to interact with the workstation 601 and its components and functions, or any other element within the system 600. This is further facilitated by the interface 104 which may include a keyboard, mouse, a joystick, a haptic device, or any other peripheral or control to permit user feedback from and interaction with the workstation 601 or system 600.

Referring to FIG. 7, a block/flow diagram shows workflow 700 for the system 600 in accordance with one illustrative embodiment. In block 702, inputs for a therapy plan are illustratively described. In block 704, a display of 2D and/or 3D images of a target anatomy in one or more views is provided on the display (619) of the graphical user interface (104). In block 706, treatment volume related inputs are provided. Examples of treatment related inputs include, e.g., an outline of a planned target volume with margins for treatment coverage inclusion as provided in block 708. In block 710, critical structures are outlined for coverage exclusion (e.g., tissues that should not be damaged by ablation). In block 712, another input type includes ablation probe related inputs. These inputs or at least default inputs can be obtained from a database. In block 714, an ablation probe or probes are selected for treatment. In block 716, ablation power/time characteristics of selected probes are set. The power/time information is based on the probe selection and is employed to derive a size and shape of the ablation regions. In other words, an ablation region of a particular size and shape may be selected based upon time/power characteristics. The sizes and shapes are completely customizable based upon temporal data for a given power.

Another input type may include entry point data in block 718. In block 720 one or more entry points for the ablation probe or probes are selected on the image. In block 722, selected ablation probes are associated with the entry point or points. Different entry points and associated probe types may provide different results. So these combinations may be provided as a form of input. In block 724, a desired number of ablations are also associated with each entry point. In block 726, criteria, weightings, margins of error, penalties, etc. are also input for therapy planning optimization.

In block 728, an optimization engine provides an optimized therapy plan based upon the inputs provided from block 702. An optimized therapy plan is computed in block 730. In block 732, a cost function or functions are employed on the inputs to optimize the plan. In block 734, the optimization engine adapts all inputs (e.g., ablation locations, sizes, shapes, power, time, inclusion regions, exclusion regions, etc.) to reach an optimal cost function value as the plan result.

In block 736, a therapy plan result is output and visualized. The output may include types and number of ablation probes, locations of entry points, locations for ablation centers, minimum number of ablations needed, minimum ablation time needed, predicted ablation metrics, collateral damage, unablated planned target volume regions, and damage to critical structures. In block 738, planned ablation volumes for each ablation are visualized on the display. In block 740, untreated tumor volume is also visualized on the display. In block 742, planned ablation probe trajectories are visualized for each entry point and ablation. In block 744, power, times, ablation size and shape, etc. are visualized for each ablation. In block 746, quantitative coverage metrics are computed (e.g., PTV coverage, etc.). In accordance with the results in block 736, a check is made in block 748 to determine if the therapy plan is acceptable. Acceptability may be based on any number of criteria, e.g., coverage, minimum number of ablations, time of procedure, etc. If unacceptable, the flow path returns to block 702 and calls for an adjustment or modification of the inputs. Replanning is performed to achieve updated results based on the new inputs.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for an ablation planning system (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An automated ablation planning system, comprising:

a user interface configured to permit selection of inputs for planning an ablation procedure, the user interface further configured to incorporate a selection of at least one of a plurality of ablation probes having structural features which provide different predetermined ablation properties and one or more combinations of ablation powers and durations applicable to selected ablation probes in the inputs to size ablation volumes, the user interface including a display for rendering internal images of a patient, the display permitting visualizations of the ablation volumes for different entry points into a body of the patient on the internal images; and an optimization engine, including a cost function and a penalty function, coupled to the user interface to receive the inputs and predetermined ablation properties and configured to output, on the user interface, an optimized therapy plan, the user interface permitting interactive planning scenarios to generate alternative planning scenarios to be considered by the optimization engine in view of a list of feasible ablation power and duration combinations based on the selected ablation probes, spatial ablation locations and temporal information for ablation so that collateral damage is reduced, coverage area is maximized and critical structures are avoided in a planned target volume, wherein the cost function and the penalty function are updated in real-time, at the user interface, as the alternative planning scenarios are generated, wherein the penalty function is defined as a function of a distance between adjacent ablation centers and as a situation where an ablation volume overlaps with a critical structure.

2. The system as recited in claim 1, wherein the cost function computes a cost based on a set of inputs and the cost is minimized to determine a set of outputs, the cost function given by:

$$C = V_{PTV} \cap (\overline{\cup V_{Ai}}) \cdot \mu_u + \overline{V_{PTV}} \cap (\cup V_{Ai}) \cdot \mu_c + \varphi \cdot \mu_P$$

where $V_{PTV}$ is a PTV volume, $V_{Ai}$ is an ith ablation volume, $\mu_u$ and $\mu_c$ are weighting factors for unablated PTV and collateral damage, respectively, symbol $\cap$ between two volumes represents a count of voxels that are set in both volumes, and symbol ∪ represents a count of voxels that are set in either volume.

3. The system as recited in claim 1, wherein the inputs include one or more of a type of ablation probe, number of ablation probes, a location of one or more entry points, planned target volume to be covered in a treatment plan, a margin of error, ablation coverage, collateral damage, regions to be excluded, ablation power, and ablation time.

4. The system as recited in claim 1, wherein the output includes types and number of ablation probes, locations of entry points, locations for ablation centers, minimum number of ablations needed, minimum ablation power or time needed, predicted ablation metrics, collateral damage, unablated planned target volume regions, and damage to critical structures.

5. The system as recited in claim 1, further comprising a database configured to store the predetermined ablation properties of the plurality of ablation probes wherein information in the database is retrievable by the user interface for the selection of at least one of a plurality of ablation probes.

6. The system as recited in claim 5, wherein the optimization engine solves an iterative non-linear optimization problem.

7. The system as recited in claim 6, wherein the non-linear optimization problem is given as:

$$\hat{\Theta} = \arg{}_\Theta \min \ C(V_{PTV}, \Sigma V_{Ai}(\Theta_i, e_i))$$

where $V_{PTV}$ is a planned target volume (PTV), $V_{Ai}$ is an ith ablation volume characterized by a parameter set $\Theta_i$ at a given skin entry point $e_i$, C is a cost function, and $\Theta_i$ is a four dimensional (4D) parameter defined as $\Theta_i = [t_x \ t_y \ t_z \ s]^T$.

8. An automated ablation planning system, comprising:
a user interface configured to permit selection of inputs for planning an ablation procedure, the user interface further configured to incorporate a selection of at least one of a plurality of ablation probes having structural features which provide different predetermined ablation properties and to incorporate ablation durations in the inputs to size the ablation volumes, the user interface including a display for rendering internal images of a patient, the display permitting visualizations of ablation volumes for different entry points into a body of the patient on the internal images, the display being configured to render internal images of a patient and provide selection controls to enable a user to select an internal image and a view of the internal image;
a database configured to store the internal images and the predetermined ablation properties for the plurality of ablation probes to assist in determining sizes and shapes for the ablation volumes for a given planned target volume by associating power and time characteristics with the sizes and shapes of the ablation volumes; and
one or more processors configured to:
receive the inputs from the user interface and the predetermined ablation properties for at least one of the plurality of ablation probes from the database,
output to the user interface an optimized therapy plan,
generate alternative planning scenarios in real time based on other user selected inputs from the user interface,
generate the alternate scenarios including at least one of:
(a) compute a cost based on the inputs and minimizing the cost to determine a set of outputs, the cost function given by:

$$C = V_{PTV} \cap (\overline{\cup V_{Ai}}) \cdot \mu_u + \overline{V_{PTV}} \cap (\cup V_{Ai}) \cdot \mu_c + \varphi \cdot \mu_p$$

where $V_{PTV}$ is a PTV volume, $V_{Ai}$ is an ith ablation volume, $\mu_u$ and $\mu_c$ are weighting factors for unablated PTV and collateral damage, respectively, symbol ∩ between two volumes represents a count of voxels that are set in both volumes, and symbol ∪ represents a count of voxels that are set in either volume, AND/OR
(b) solve an iterative non-linear optimization problem given as:

$$\hat{\Theta} = \arg{}_\Theta \min \ C(V_{PTV}, \Sigma V_{Ai}(\Theta_i, e_i))$$

where $V_{PTV}$ is a planned target volume (PTV), $V_{Ai}$ is an ith ablation volume characterized by a parameter set $\Theta_i$ at a given skin entry point $e_i$, C is a cost function, and $\Theta_i$ is a four dimensional (4D) parameter defined as $\Theta_i = [t_x \ t_y \ t_z \ s]^T$.

9. A method for planning an ablation procedure, comprising:
displaying an internal image of a patient on a display of a user interface;
selecting at least one of a plurality of ablation probes having structural features which provide different predetermined ablation properties for performing an ablation procedure using the user interface;
selecting a point or points of entry into a body of the patient for the at least one of the plurality of ablation probes on the internal image;
applying a cost function and a penalty function to minimize a cost for the predetermined ablation properties of the at least one selected plurality of ablation probes, the selected point or points of entry, time and power information to determine sizes and shapes of ablation volumes, wherein the cost function is given by:

$$C = V_{PTV} \cap (\overline{\cup V_{Ai}}) \cdot \mu_u + \overline{V_{PTV}} \cap (\cup V_{Ai}) \cdot \mu_c + \varphi \cdot \mu_p$$

where $V_{PTV}$ is a PTV volume, $V_{ai}$ is an ith ablation volume, $\mu_u$ and $\mu_c$ are weighting factors for unablated PTV and collateral damage, respectively, symbol ∩ between two volumes represents a count of voxels that are set in both volumes, and symbol ∪ represents a count of voxels that are set in either volume; and
outputting, on the user interface, an optimized therapy plan, the user interface permitting interactive planning scenarios to generate alternative planning scenarios in view of at least a list of feasible ablation power and duration combinations based on the selected ablation probes to reduce collateral damage, maximize coverage area and avoid critical structures in a planned target volume, wherein the cost function and the penalty function are updated in real-time, at the user interface, as the alternative planning scenarios are generated.

10. The method as recited in claim 9, wherein the penalty function is defined as a function of a distance between adjacent ablation centers and as a situation where an ablation volume overlaps with a critical structure.

11. The method as recited in claim 9, wherein the cost function and the penalty function further consider a margin of error, ablation coverage, collateral damage, regions to be excluded, ablation power, and ablation time.

12. The method as recited in claim 9, wherein the optimized therapy plan includes types and number of ablation probes, locations of entry points, locations for ablation centers, minimum number of ablations needed, minimum ablation power or time needed, ablation metrics, collateral damage, unablated planned target volume regions, and damage to critical structures.

13. The method as recited in claim 9, further including solving an iterative non-linear optimization problem.

14. A method for planning an ablation procedure, comprising:
   displaying an internal image of a patient on a display of a user interface;
   selecting from a plurality of ablation probes having structural features which provide different predetermined ablation properties for performing an ablation procedure using the user interface;
   selecting a point or points of entry into a body of the patient for at least one of the plurality of ablation probes on the internal image;
   solving an iterative non-linear optimization problem given as:

$\hat{\Theta}\text{arg }_\Theta\text{min }C(V_{PTV}, \Sigma V_{Ai}(\Theta_i, e_i))$ where $V_{PTV}$ is a planned target volume (PTV), $V_{Ai}$ is an ith ablation volume characterized by a parameter set $\Theta_i$ at a given skin entry point $e_i$, C is a cost function, and $\Theta_i$ is a four dimensional (4D) parameter defined as $\Theta_i=[t_x\ t_y\ t_z\ s]^T$;

outputting, on the user interface, an optimized therapy plan, the user interface permitting interactive planning scenarios to generate alternative planning scenarios in view of at least a list of feasible ablation power and duration combinations based on the selected ablation probes to reduce collateral damage, maximize coverage area and avoid critical structures in a planned target volume, wherein the non-linear optimization problem is updated in real-time, at the user interface, as the alternative planning scenarios are generated.

15. The method as recited in claim 14, wherein the non-linear optimization problem includes applying a cost function and a penalty function.

* * * * *